United States Patent
Chandler et al.

(10) Patent No.: US 6,345,622 B1
(45) Date of Patent: Feb. 12, 2002

(54) METHOD OF USING A DUAL REFRACTIVE DRAPE

(75) Inventors: Lamar R. Chandler, St. Petersburg; Tony D. Quattrone, Sarasota, both of FL (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 0 days.

(21) Appl. No.: 09/506,877

(22) Filed: Feb. 18, 2000

(51) Int. Cl.⁷ .................................................. A61B 19/00
(52) U.S. Cl. ........................................ 128/849; 128/856
(58) Field of Search ................................... 128/849–856

(56) References Cited

U.S. PATENT DOCUMENTS

| | | | |
|---|---|---|---|
| 4,869,271 A | 9/1989 | Idris | 128/853 |
| 4,966,168 A | 10/1990 | Glassman | 128/853 |
| 5,038,798 A | 8/1991 | Dowdy et al. | 128/853 |
| 5,042,507 A | 8/1991 | Dowdy | 128/849 |
| 5,140,996 A * | 8/1992 | Sommers | 128/853 |
| 5,140,997 A | 8/1992 | Glassman | 128/849 |
| 5,191,897 A | 3/1993 | Meshel | 128/745 |
| 5,213,114 A * | 5/1993 | Bailey, Jr. | 128/849 |
| 5,225,236 A | 7/1993 | Keusch et al. | 428/77 |
| RE34,512 E | 1/1994 | Dowdy et al. | 128/853 |
| 5,345,946 A | 9/1994 | Butterworth et al. | 128/853 |
| 5,361,780 A * | 11/1994 | Kellan | 128/853 |
| 5,632,284 A | 5/1997 | Graether | 128/849 |
| 5,975,082 A | 11/1999 | Dowdy | 128/849 |
| 6,070,587 A * | 6/2000 | Levitt | 128/853 |

OTHER PUBLICATIONS

3M Health Care—Advertisement "3M Steri–Drape 1022 Refractive Drape" 3M Health Care—Advertisement "3M Steri–Drape 1022 Refractive Drape"—Ordering Information Medical Concepts Development, Inc.—Advertisement "Refractive Drape D1022" BD—Advertisement—"We've Got You Covered".

* cited by examiner

Primary Examiner—Micahel A. Brown
(74) Attorney, Agent, or Firm—Alan W. Fiedler

(57) ABSTRACT

Method of using a drape is described for use in various ophthalmic surgeries including refractive eye surgery. The drape can be configured in at least sixteen different ways for both single or bilateral eye surgical procedures. The drape includes an adhesive liner that acts as a cover for the non-surgical eye. A tent portion is also provided that allows the patient to blink or comfortably keep open the covered non-surgical eye. Allowing the patient to blink or keep open the covered non-surgical eye gives support or assists in fixation of the surgical eye. The drape is also positions the apertures are on the lower half of the drape in order to leave the bottom of the nose and mouth uncovered for patient comfort. An adhesive liner may be provided with the drape for allowing coverage of the non-surgical eye.

16 Claims, 15 Drawing Sheets

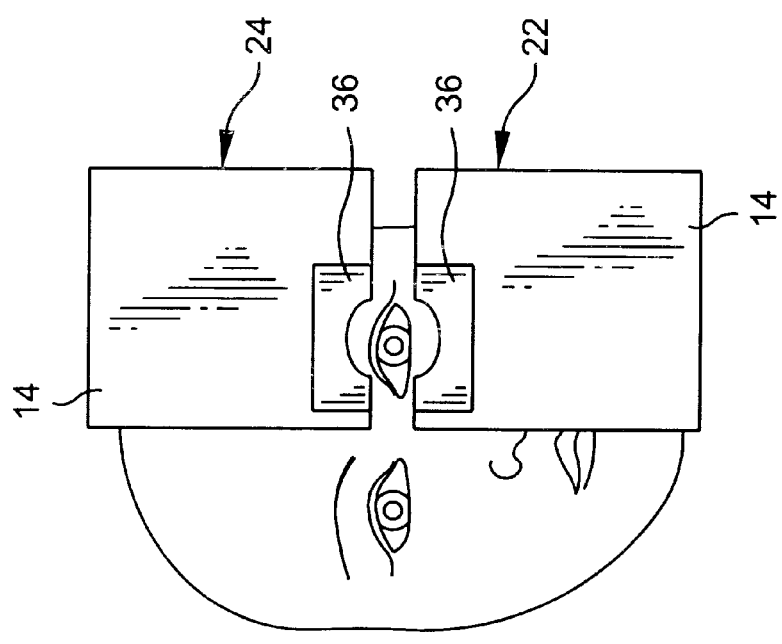
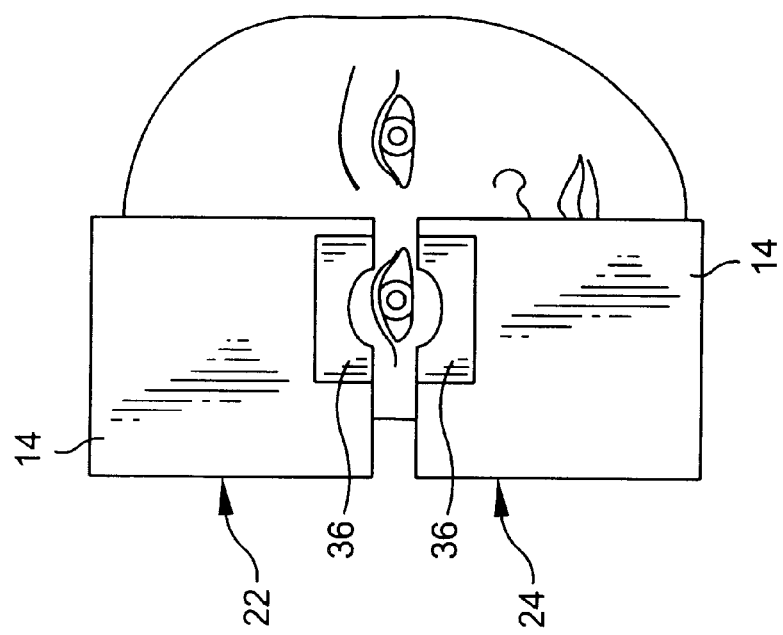

METHOD OF USING A DUAL REFRACTIVE DRAPE

FIELD OF INVENTION

This invention relates generally to a method of using a medical device in ophthalmic surgery. More particularly, this invention relates to a method of using a dual refractive drape that can be used in refractive eye surgery as well as other eye surgeries and configured in sixteen different ways for both single or bilateral eye surgical procedures. The drape includes an adhesive liner that acts as a cover for the non-surgical eye and a tent portion that allows the patient to blink or comfortably keep open the non-surgical eye, which is needed for eye fixation.

BACKGROUND OF THE INVENTION

Surgical drapes are well known in the medical arts as being used to maintain a sterile environment during surgery. Drapes also assist in preventing foreign matter and organisms from entering the surgical area. Surgical drapes are made in a wide variety of sizes and shapes for covering portions of the body during surgery. In ophthalmic surgical procedures, eye drapes are frequently used to surround and protect the eyeball. A traditional eye drape typically includes a base sheet with a fenestration to expose the eye that is to undergo surgery.

In recent years, refractive surgery has become an increasingly popular surgical procedure for the eye. Refractive surgery refers to a range of surgical procedures using knives, lasers, or some combination to alter the cornea resulting in structural changes in the cornea's curvature. The resultant change in the cornea's shape often produces a significant change in its refractive power. Thus, the use of glasses or contacts to correct vision is minimized or totally eliminated.

Various types of refractive surgery include radial keratectomy (RK), automated lamellar keratoplasty (ALK), photorefractive keratectomy (PRK), and laser assisted in-situ keratomileusis (LASIK). Of these surgical procedures, LASIK is considered the fastest growing refractive procedure in the United States.

In LASIK surgery, a microkeratome blade is typically used. The microkeratome is a surgical instrument used to cut and fold back a thin superficial layer of the cornea. This layer is called the corneal cap. After the corneal cap is formed, the re-shaping of the cornea is accomplished with a laser. The bed of the cornea under the corneal cap is flattened or re-molded to correct for areas of shortsightedness, farsightedness, and astigmatism. After the central cornea is re-molded by the laser, the cap is folded back over the central cornea and allowed to heal in place without any need for sutures. The patient is very comfortable after the surgery and can return to normal activities by the next day. Generally, sight is restored within that following day.

During LASIK surgery, the patient can be exposed to scatter rays from the laser or projectile debris from laser ablation or other tissue removal procedures. Some prior art ophthalmic drapes can sufficiently protect the patient from the debris. However, these prior art drapes often lack the material characteristics required to reflect scatter rays from the laser.

Prior art ophthalmic drapes made of a laser reflective material still lack the flexibility of being used in other refractive procedures that require various draping configurations. Additionally, prior art drapes used specifically for refractive surgery lack the drape configuration necessary in other similar vision corrective surgical procedures. Such surgeries may include implantation of phakic intraocular lenses, implantation of intrastromal corneal ring segments, and phototherapeutic keratectomy (PTK). Thus, a specific prior art drape would have to be used for each specific surgery. This type of prior art drape would contribute to decreased economic efficiencies, increased medical waste, and increased healthcare costs.

Finally, prior art ophthalmic drapes do not have the ability or features to cover the non-surgical eye, and provide the flexibility of various draping configurations while giving the patient the ability to blink or comfortably keep open the non-surgical eye. Keeping the non-surgical eye open is preferred during refractive surgery because the patient can not lose eye fixation during laser ablation. If fixation of the surgical eye does not occur and the eye moves, the surgery may result in an off-centered ablation of the operated eye and impaired vision.

In summary, the use of prior art ophthalmic drape designs have many disadvantages. First, many prior art drapes do not have the material characteristics required to reflect scatter rays from the laser during LASIK refractive surgery. Second, those prior art drapes that are made of a laser reflective material still lack the flexibility of being used in any refractive procedure or other ophthalmic surgery that may require various draping configurations. Therefore, specific prior art drapes would have to be used for each specific surgery thereby increasing medical waste, healthcare costs and decreasing economic efficiencies. Third, prior art ophthalmic drapes do not have the ability or features to cover the non-surgical eye and provide the flexibility of various draping configurations. Prior art ophthalmic drapes that do cover the non-surgical eye do not give the patient the ability to blink or comfortably keep open the non-surgical eye that is important for eye fixation.

Therefore, a need still exists in the art for the use of an ophthalmic drape to be configured in various shapes and physical arrangements to be used in many eye surgical procedures including refractive surgery. The use of the improved drape should provide protection for the patient from scatter rays and projectile debris due to laser ablation. The method of using the drape should also have a step for covering the non-surgical eye and allowing the patient to blink the non-surgical eye in comfort to facilitate eye fixation.

SUMMARY OF THE INVENTION

The present invention avoids the disadvantages of the prior art by allowing a method of using an ophthalmic drape that can be configured in various shapes and physical arrangements for use in many eye surgical procedures including refractive surgery. The method of using the improved drape provides protection to the patient and surgeon from scatter rays and projectile debris due to laser ablation. The method also includes the steps of covering the non-surgical eye and allowing the patient to blink and keeping the non-surgical eye open in comfort to facilitate eye fixation.

Accordingly, there is provided in the present invention a method of using a dual refractive drape including the steps of holding a drape of the type having a sheet that includes a top, a bottom, a right aperture and a left aperture. The sheet further defines at least one first perforation and at least one-second perforation such that the first perforation is positioned between and about the right and left apertures. The second perforation is positioned so that the apertures are divided by the second perforation. It is the positioning of the first and second perforations that allows the sheet to be configured in various shapes and physical arrangements.

After holding the drape and configuring the drape in one of at least sixteen different configurations to meet the specific surgery needs, placement of the drape on the patient is then done. The steps of covering the non-surgical eye and facilitating eye fixation of the surgical eye is provided by an adhesive liner and by providing the sheet with a tent portion formed about the second perforation. The tent portion provides clearance between the eye and the sheet. The step of protecting the patient and surgeon from scatter rays caused by the laser is accomplished by the drape being made of a laser reflective material.

BRIEF DESCRIPTION OF THE DRAWINGS

FIG. 13 is a top view illustrating the sheet covering only the right eye using both the right and left upper portions of the sheet.

FIG. 14 is a top view illustrating the sheet covering only the left eye using both the left and right upper portions of the sheet.

DETAILED DESCRIPTION

Figure 1:
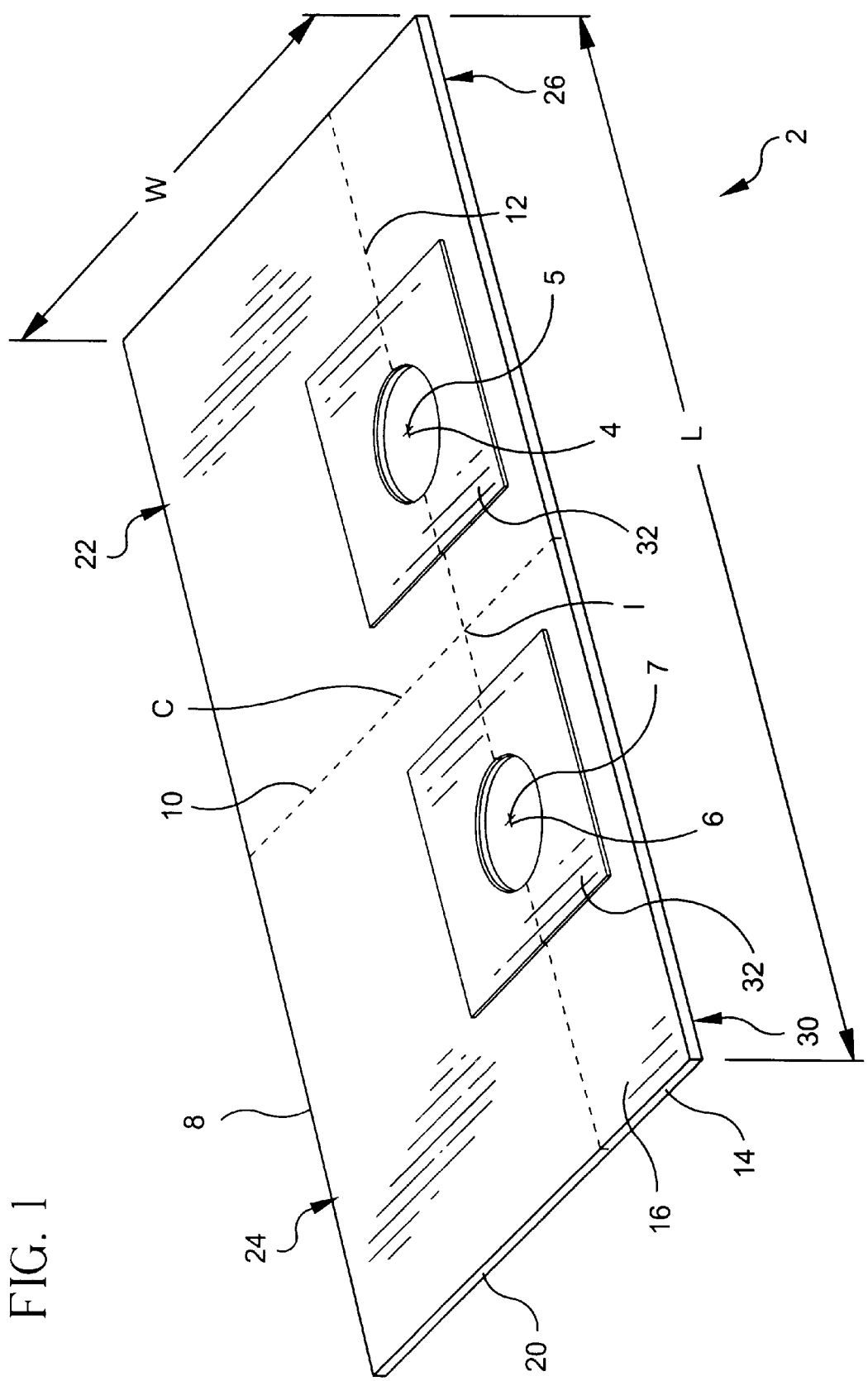
FIG. 1 is a bottom perspective view of the present invention.

A dual refractive drape in accordance with the subject invention is identified generally by the numeral 2 in FIGS. 1–23. Drape 2 includes a sheet 8 having a top 14, a bottom 16, and a side 20. The drape further defines a right aperture 4 and a left aperture 6. The apertures are used to expose the eye for the appropriate surgical procedure. Preferably, the apertures are oval shaped to match the curvature of the eyes. However, other such shapes could be used as well. Such shapes include circular, elliptical, semi-circular, triangular, rectangular, squared and any other polygonal shape.

Apertures 4 and 6 are sized to expose only a small area of the eye to be operated on so that the remainder of the eye can be protected during surgery. Accordingly, the apertures have an aperture length and an aperture width that allow only a small amount of the eye's area to be exposed during surgery. To facilitate such a characteristic, the aperture length is preferably no greater than 1 9/16" and the aperture width is no greater than 1 1/16". In addition, the apertures further include a right eye center point 5 and a left eye center point 7 for positioning the apertures on sheet 8 such that the apertures are centered on the patient's eye during surgery. Left eye center point 7 and right eye center point 5 are further preferably equidistant from a first perforation 10. This positioning allows centering of the sheet on the patient.

Figure 4:
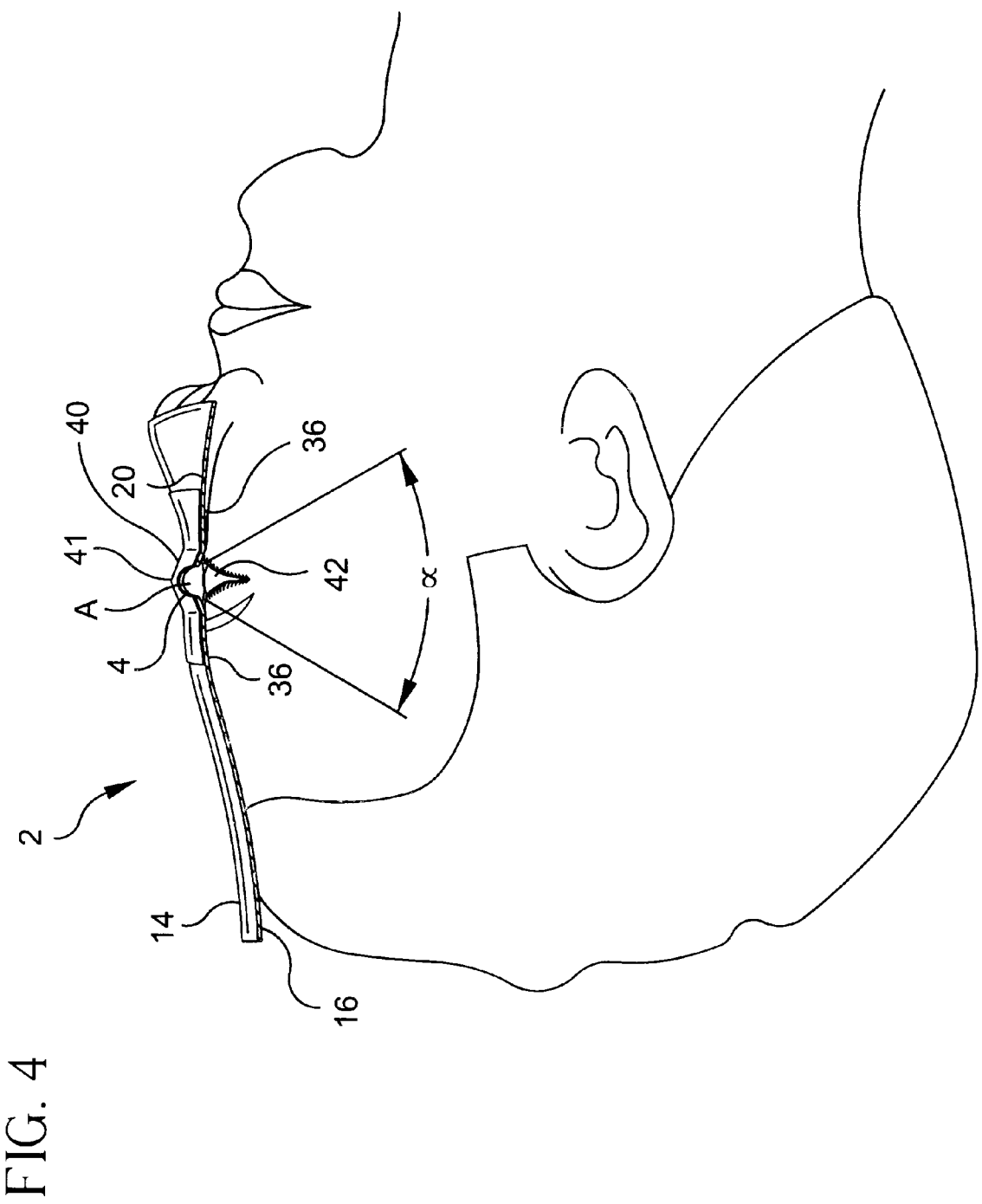
FIG. 4 is a side view of the present invention applied to a patient's eye.
Figure 6:
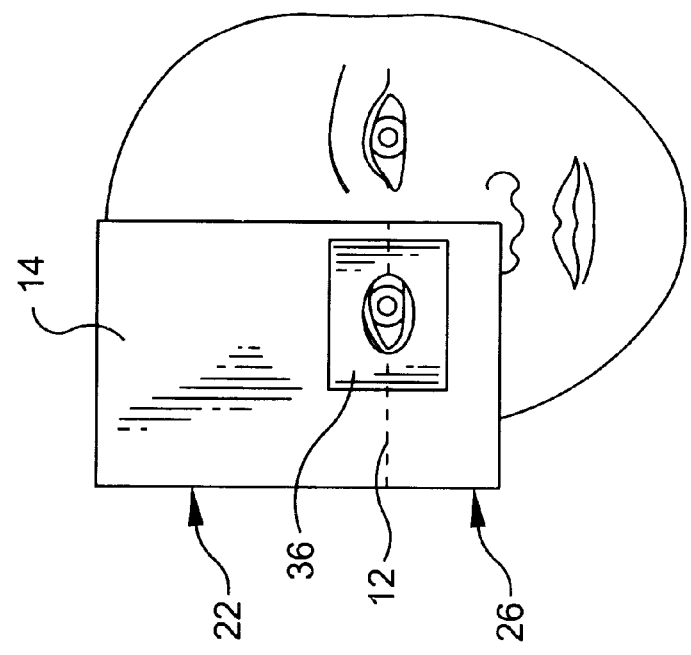
FIG. 6 is the view in FIG. 5 with the sheet covering only the right eye.

Sheet 8 further includes a center point "C" as shown in FIG. 1. The apertures are preferably positioned on the sheet such that they are offset from the center point "C". However, it is within the scope of the invention for the apertures not to be offset form center point "C". When the apertures are offset form center point "C", this position allows the sheet to have more area for protection of the patient's head and clearance of the patient's mouth and nose as shown in FIG. 4.

Sheet 8 can be any geometric shape, but is preferably rectangular in shape. The sheet is preferably made of a material that is resistant or reflective to laser scatter for protecting the patient and surgeon from laser scatter or projectile debris caused by laser ablation. Preferably, the material is also capable of having a dull mat finish and is selected from the group consisting of woven polyethylene, polypropylene, thermoplastic polymers, surgical grade paper, and various combinations of the materials previously mentioned. The sheet further includes a width "W" and a length "L" that allows the drape to sufficiently provide a sterile field and protection against scatter rays and debris while leaving the bottom of the patient's nose and mouth uncovered for patient comfort. To accommodate this feature, width "W" is preferably between about 9½" to about 10" and length "L" is between about 15¾" to about 16¼" long.

Sheet 8 further defines at least one first perforation 10 and at least one-second perforation 12. Preferably, the first perforation is vertical and the second perforation is horizontal as shown in FIG. 1. However, the perforations can be at any angle that allows the sheet to be configured in various shapes and physical arrangements.

With respect to the first perforation, the apertures are substantially linear and symmetrical to the first perforation.

Preferably, the second perforation bisects the apertures in equal portions. However, it is within the scope of the invention for the second perforation to divide the apertures into unequal halves.

FIG. 1 also illustrates how the perforations form an intersection generally identified as the letter "I". It is also within the scope of the invention for the perforations not form an intersection. Examples of alternate embodiments with no intersection would be when the perforations are running parallel to each other, when the perforations are running adjacent to each other, and when the perforations simply do not meet. However, it is preferred that the first and second perforations do form intersection "I". It is also preferable that the first and second perforations are perpendicular to each other. However, the perforations may be positioned at any angle relative to each other to perform the function of the present invention, which is to allow the sheet to be configured in various shapes and physical arrangements. At least sixteen (16) different arrangements are allowed with the present invention. This flexibility allows the drape to be used in many different eye surgeries for both single or bilateral eye surgical procedures including refractive surgery.

Preferably, perforation 10 is positioned between and about the right and left apertures. Perforation 12 is preferably positioned such that the apertures are divided by perforation 12. This arrangement and placement of perforations allows the sheet to be configured in various shapes and physical arrangements that will later be described in detail.

Figure 2:
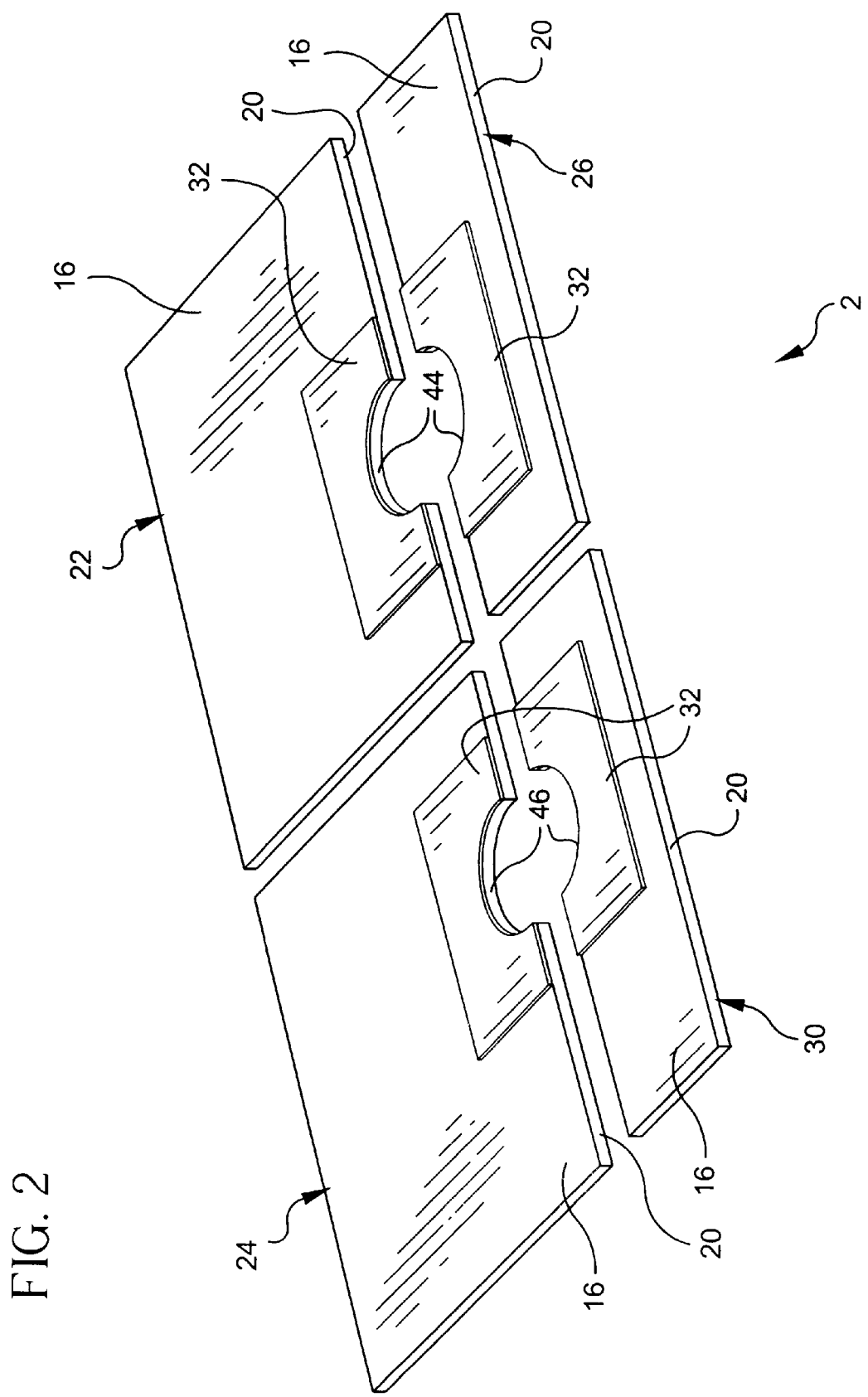
FIG. 2 is the view in FIG. 1 with the sheet fully separated along the perforations.

FIG. 2 illustrates how the sheet can be separated along the perforations, which allow the drape to be positioned on the patient in various shapes and physical arrangements. Preferably, perforation 10 equally divides the sheet vertically and perforation 12 divides the sheet perpendicularly to perforation 10, or horizontally, in unequal portions. This versatility of the drape allows at least sixteen different draping configurations. This feature allows the drape to be used in many different eye surgeries including many refractive eye surgeries such as radial keratectomy (RK), automated lamellar keratoplasty (ALK), photorefractive keratectomy (PRK), and laser assisted in-situ keratomileusis (LASIK). When the sheet is separated, a right eye cutaway portion 44 and a left eye cutaway portion 46 is formed as shown in FIG. 2. The cutaway portions outline the eyes and provide protection as well as access to the eyes.

When the sheet is separated, an upper right portion 22, an upper left portion 24, a lower right portion 26 and a lower left portion 30 are also formed. The upper portions are preferably greater in area than the lower portions to provide protection to the patient's head area. The lower portions are smaller in area as compared to the upper portions so that the bottom of the mouth and nose area are left uncovered as shown in FIG. 4.

Figure 3:
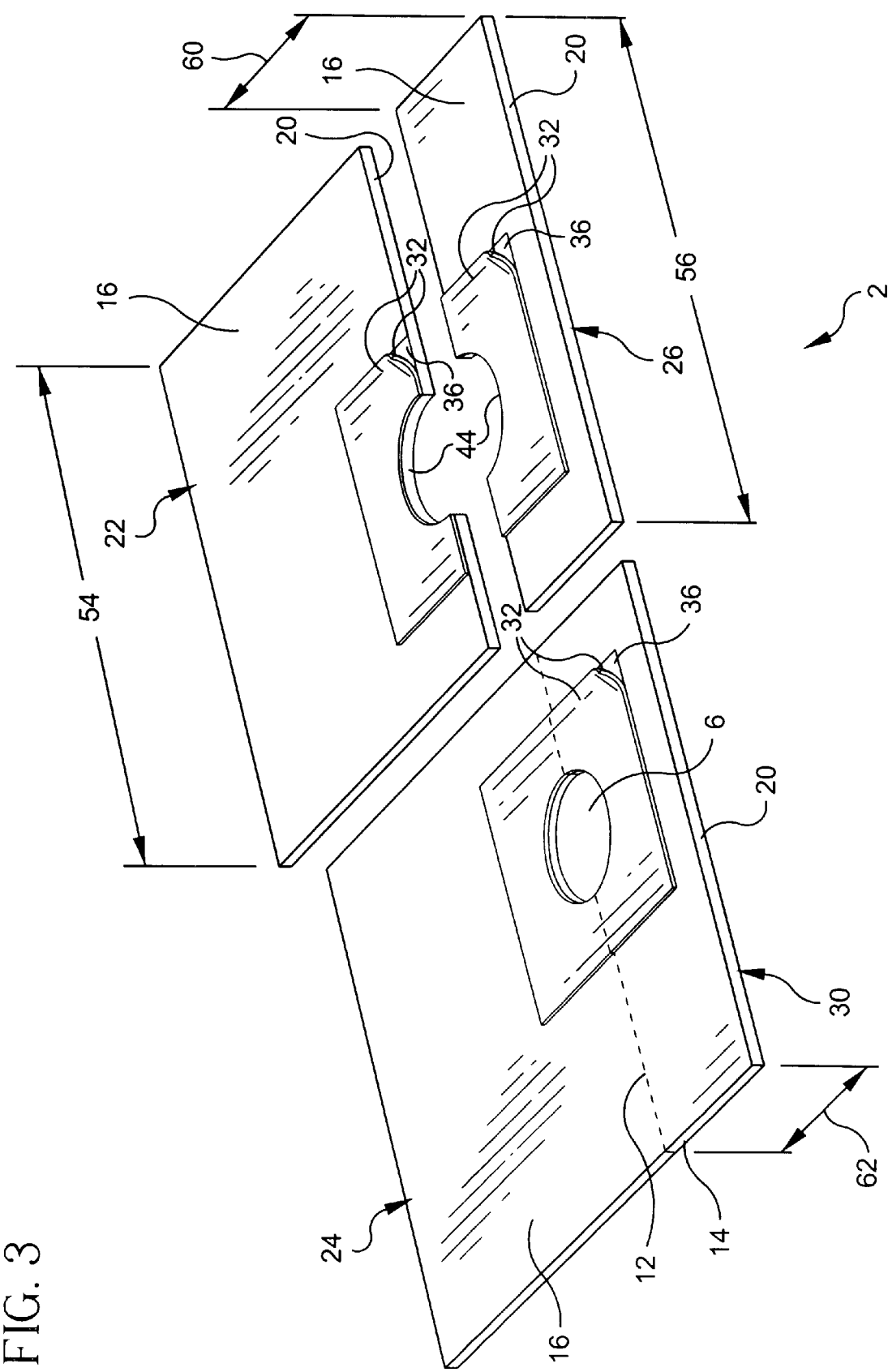
FIG. 3 is the view in FIG. 1 with the sheet partially separated along the perforations and illustrating the removal of the peel cards to expose the adhesive layer.

The upper and lower portions further include an upper portion length 54 and a lower portion length 56 as indicated in FIG. 3. Preferably the portion lengths are equal, however they need not be for the invention to function. The upper and lower portion lengths are preferably between about 7⅞" to about 8⅛". The right and left lower portions further include a right lower portion width 60 and a left lower portion width. These widths are preferably equivalent however they need not be for the present invention to function according to its inventive features. These widths are preferably between about 2⅛" to about 2⅜". These dimensions assist the drape in having greater drape coverage area to cover the head and eyes while giving the mouth and bottom of the nose open access for patient comfort.

Adverting to FIG. 3, shown is an adhesive layer 36 disposed around the apertures for adhering the sheet to the patient and securing the apertures in position around the patient's eyes. Preferably, the adhesive layer is disposed on the bottom of the sheet. There are many methods of applying the adhesive to the sheet and types of adhesives known to those skilled in the art. Such methods include spray coating, dipping, roller applied, and stamping. Types of adhesives would include, but not limited to, medical grade adhesives, cyanoacrylate based adhesives, and epoxy based adhesives.

Adhesive layer 36 further has a plurality of removable peel cards 32 disposed over the adhesive layer to prevent premature adhesion. As shown in FIG. 3, the peel card is divided by the second perforation. This division allows the adhesive layer to be used on both the upper and lower portions of the sheet.

A tent portion 40 as shown in FIG. 4 is formed about the second perforation. The tent portion provides clearance between the eye and the sheet. This feature allows the patient to blink the surgical eye which facilitates eye fixation. Eye fixation or the ability to position the eye in a fixed position is needed during eye surgery.

Also formed by tent portion 40 is a clearance portion "A". Clearance portion "A" provides the clearance between the patient's eyes and the sheet. The clearance portion can be selectively increased or decreased merely by changing angle "α" formed at an apex 41 of tent portion 40.

Figure 5:
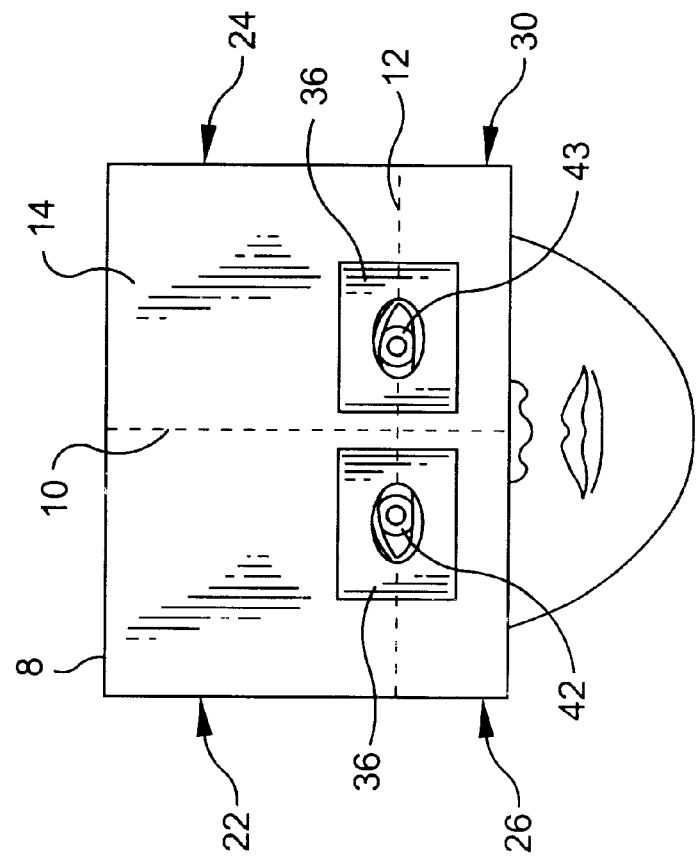
FIG. 5 is top view of the present invention covering both the right and left eyes.
Figure 8:
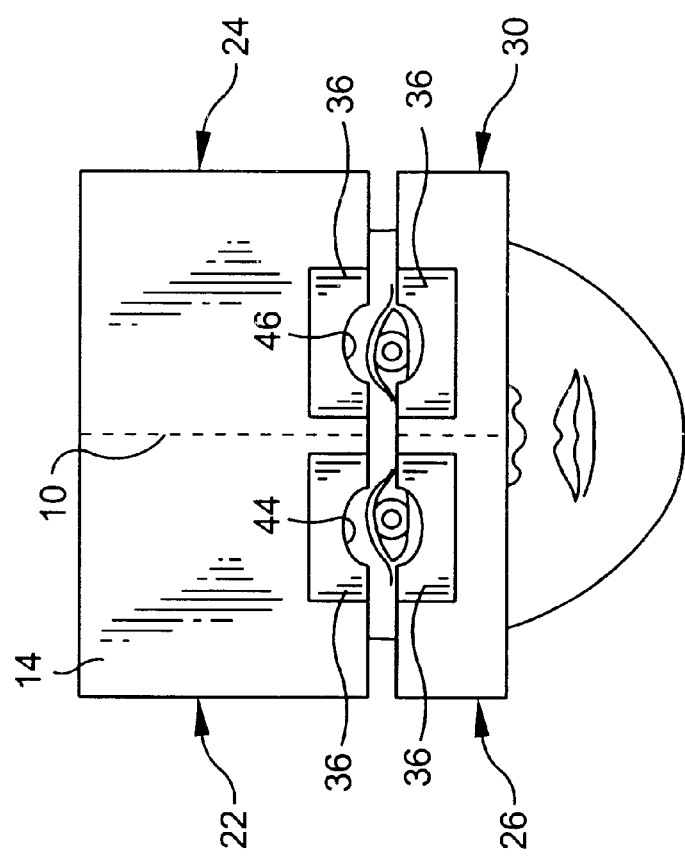
FIG. 8 is the view in FIG. 5 with the sheet covering both the right and left eyes and separated along the second perforation.
Figure 7:
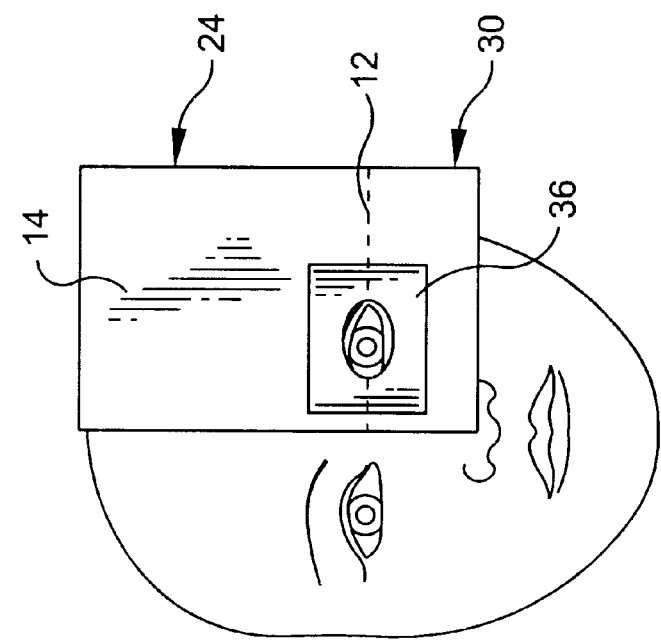
FIG. 7 is the view in FIG. 5 with the sheet covering only the left eye.
Figure 10:
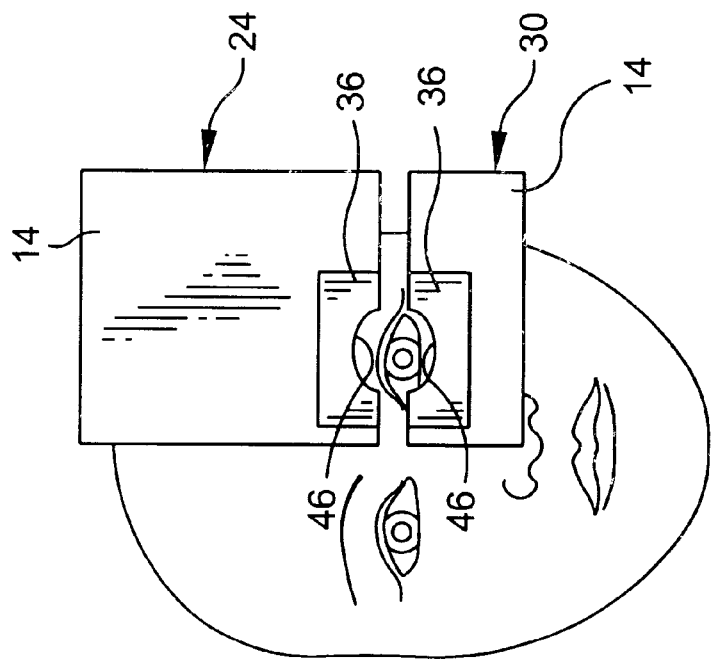
FIG. 10 is the view in FIG. 7 with the sheet separated along the second perforation.
Figure 9:
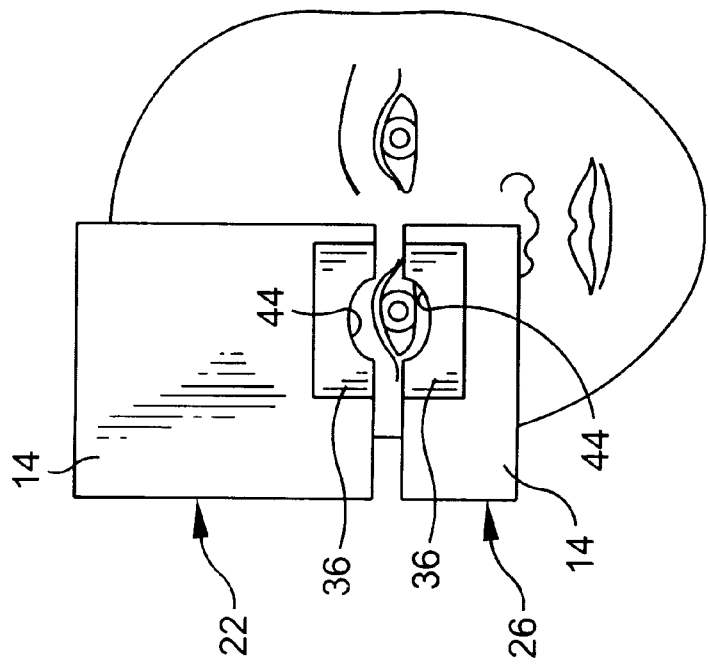
FIG. 9 is the view in FIG. 6 with the sheet separated along the second perforation.
Figure 12:
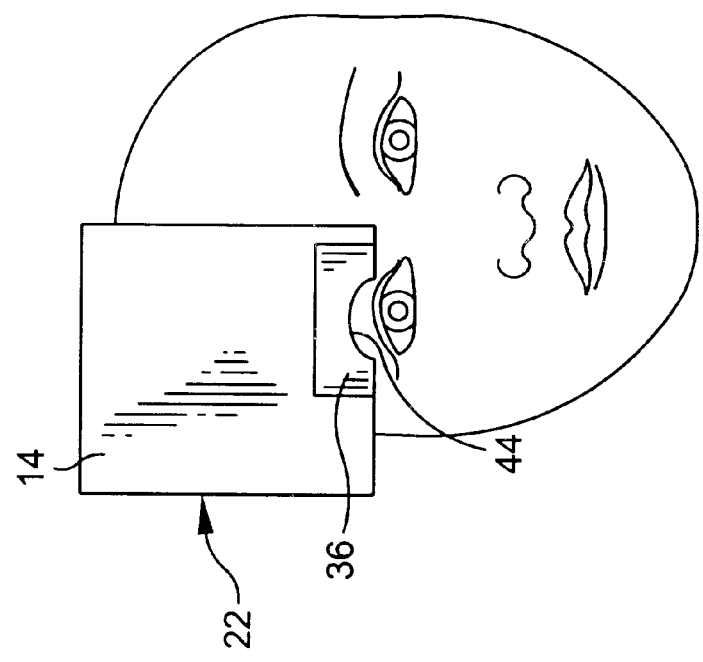
FIG. 12 is a top view of the present invention with the sheet covering only the right eye using only the upper right portion of the sheet.
Figure 11:
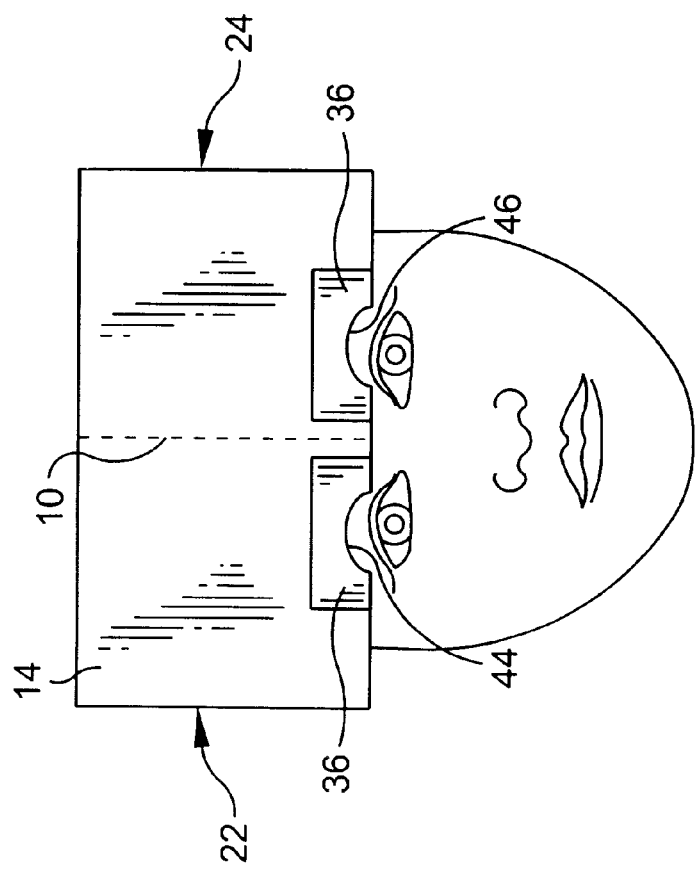
FIG. 11 is a top view of the present invention with the sheet covering both the right and left eyes using only the right and left upper portions of the sheet.
Figure 15:
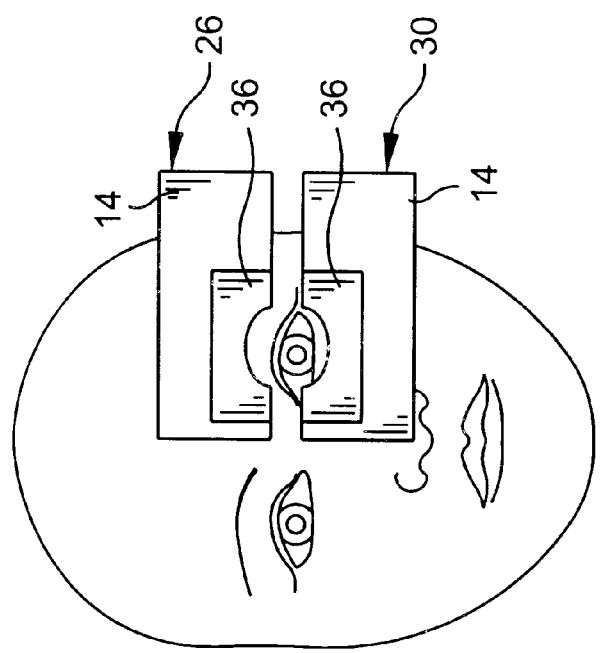
FIG. 15 is a top view showing the sheet covering only the right eye using both the right and left lower portions of the sheet.
Figure 16:
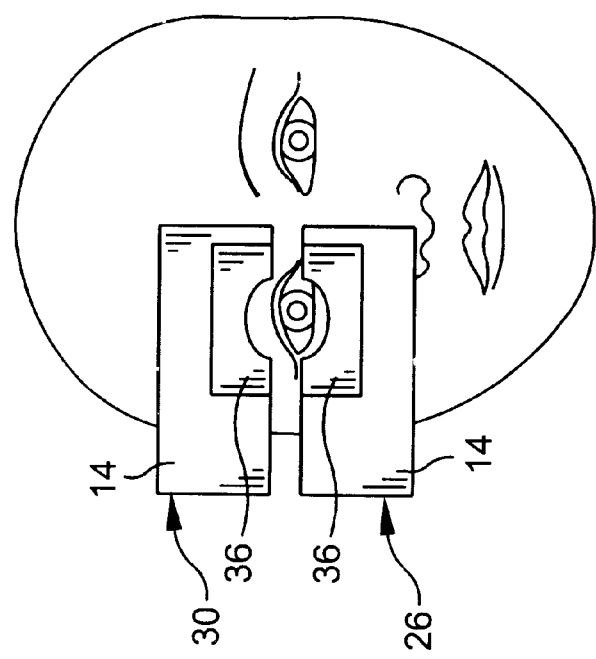
FIG. 16 is a top view showing the sheet covering only the left eye using both the left and right lower portions of the sheet.
Figure 17:
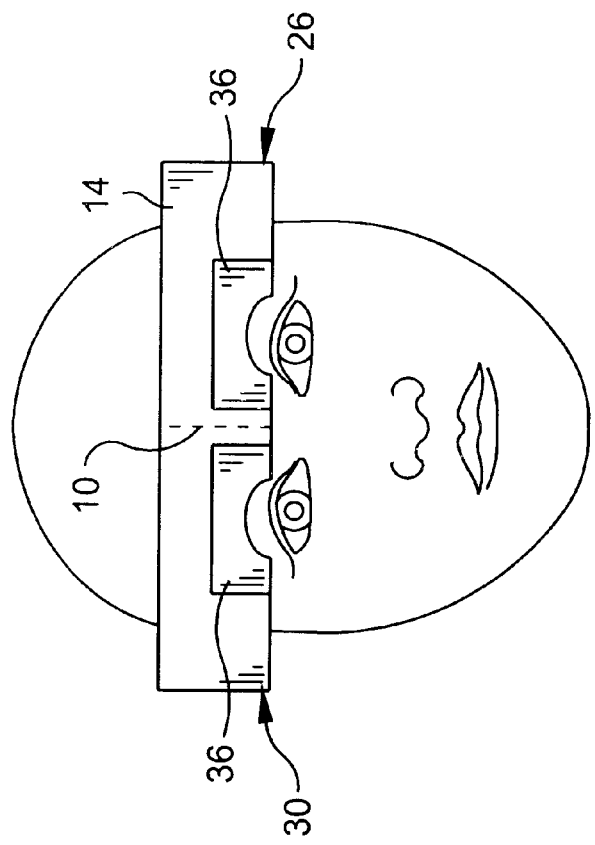
FIG. 17 is a top view of the sheet covering only the left eye using only the upper left portion of the sheet.
Figure 18:
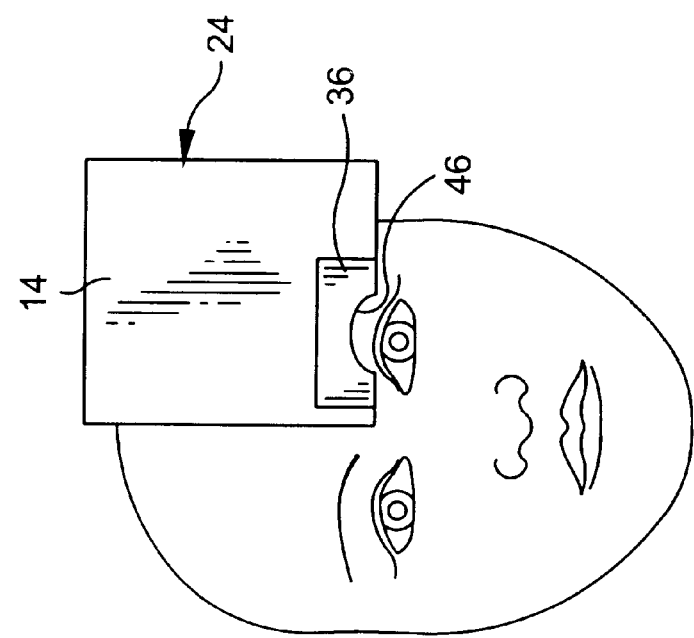
FIG. 18 is a top view of the sheet covering both eyes using only the right and left lower portions of the sheet.
Figure 20:
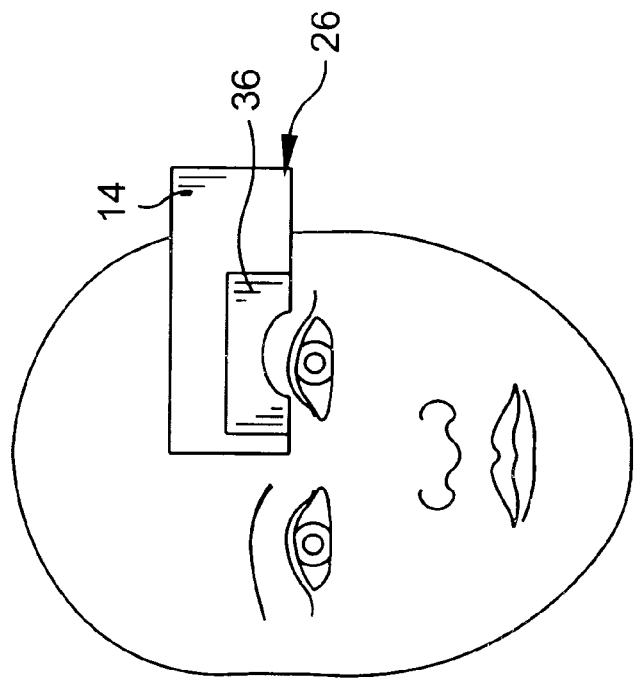
FIG. 20 is a top view illustrating the sheet covering only the left eye using only the right lower portion of the sheet.
Figure 19:
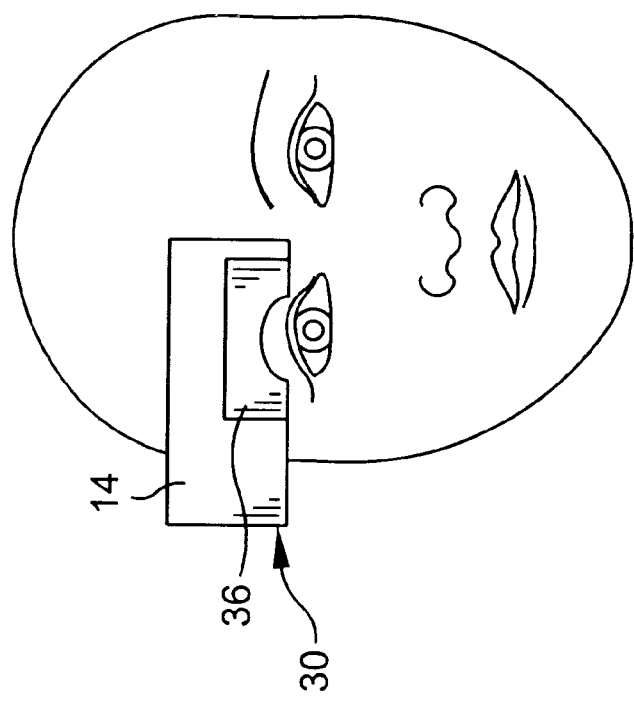
FIG. 19 is a top view illustrating the sheet covering only the right eye using only the left lower portion of the sheet.

Adverting to FIGS. 5–20, shown are at least sixteen different configurations of the sheet on the patient. By separating the sheet along the first and/or the second perforations, many different shapes and physical arrangements of the sheet can be configured. This allows the practitioner to use a single drape for both single and bilateral eye surgical procedures. Most prior art drapes have only a single aperture. Thus, in order to perform a bilateral procedure using a prior art drape, the practitioner must obtain an additional drape to proceed on operating on the opposing eye. As shown in FIG. 5, a right eye 42, and a left eye 43 can both be operated on using the same drape.

Figure 21:
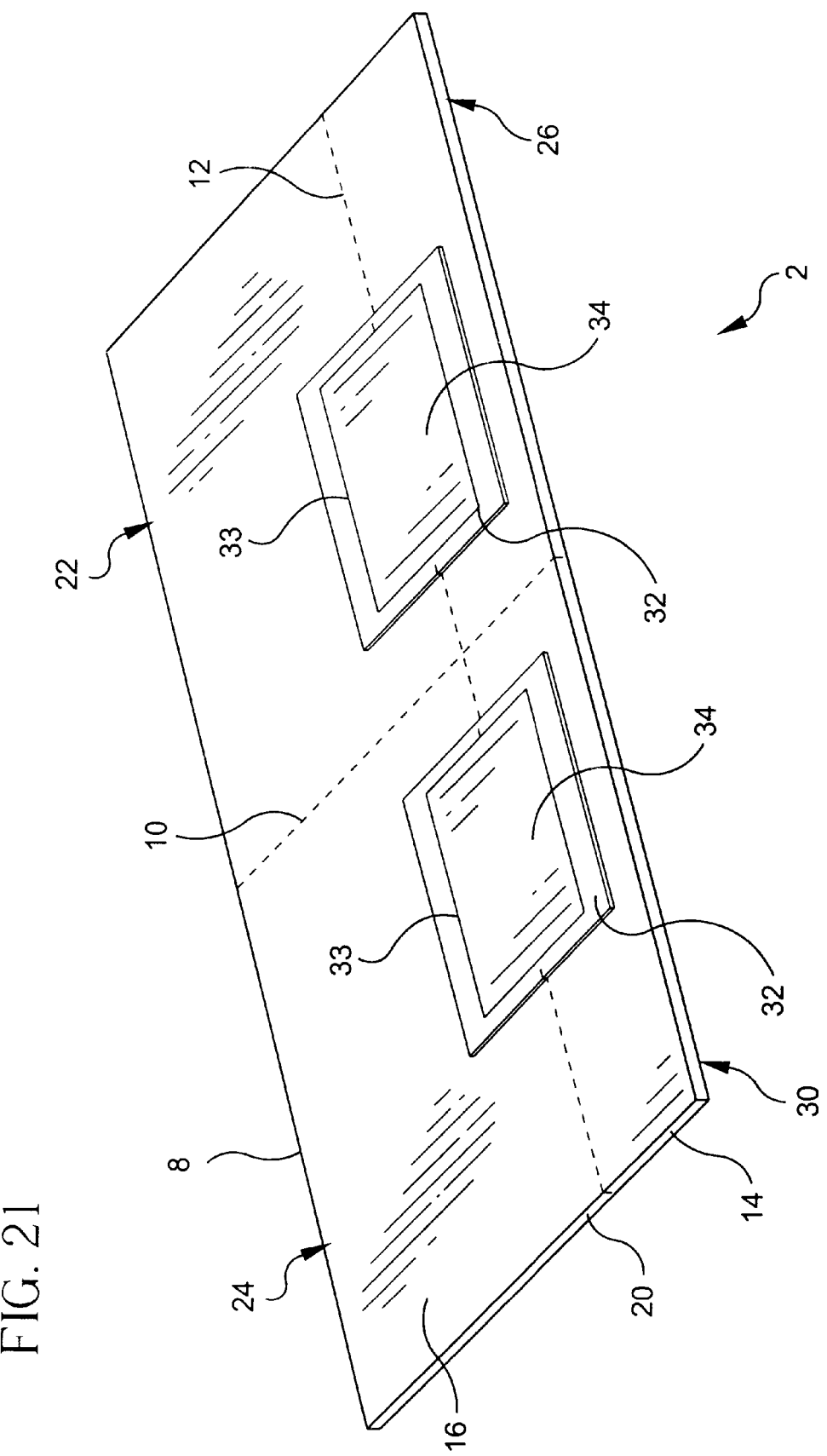
FIG. 21 is the bottom perspective view of FIG. 1 with the adhesive liners attached to the sheet.
Figure 22:
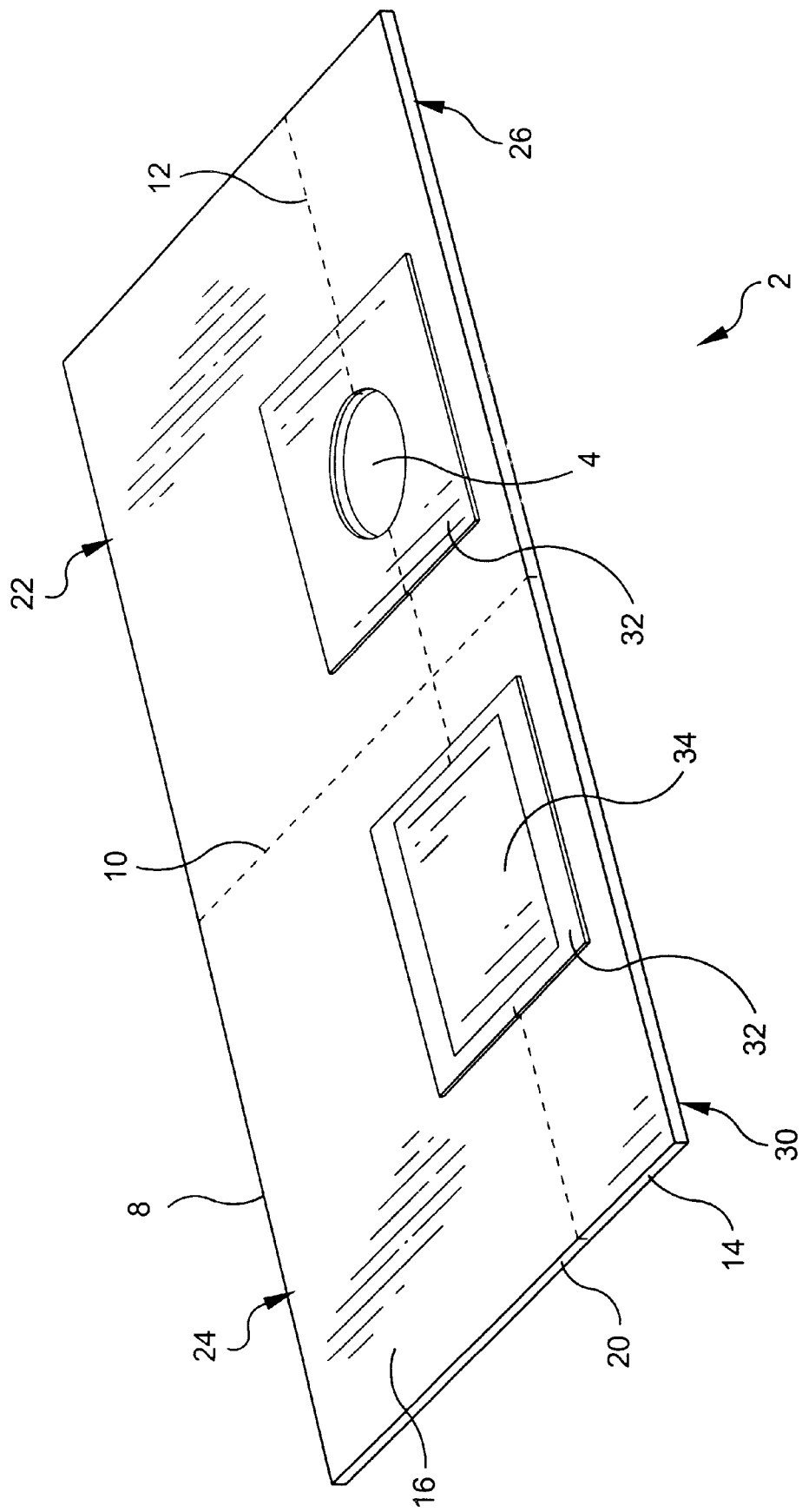
FIG. 22 is the view in FIG. 21 with one of the adhesive liners removed exposing the right eye aperture.
Figure 23:
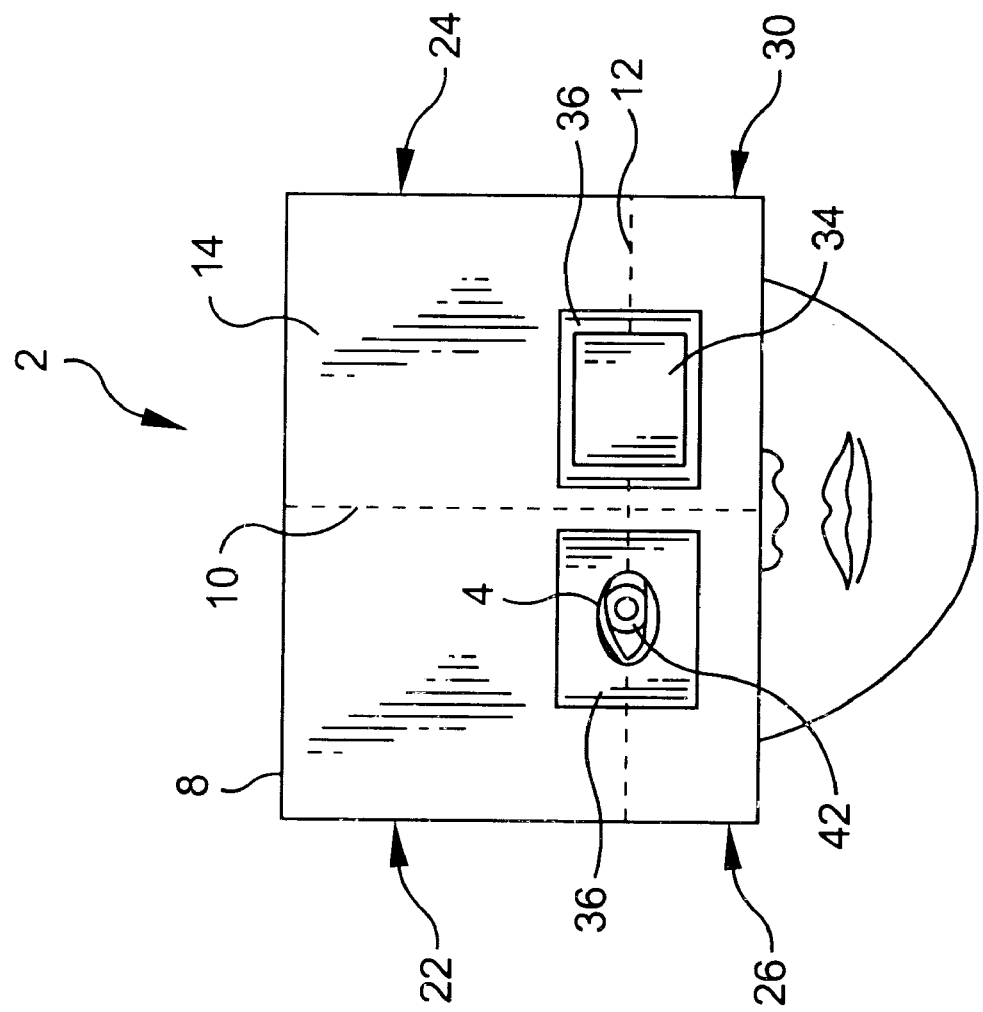
FIG. 23 is a top view of the sheet in FIG. 22 applied to a patient and exposing the right eye while covering the left eye.

FIGS. 21–23 illustrate the sheet with a plurality of adhesive liners 34 disposed over the apertures. Preferably, the liners are disposed on the opposite side of the sheet as the peel cards and adhesive layer are disposed. However, it is within the scope of the present invention for the liners to be on the same side as the peel cards and adhesive layer. Thus, preferably when the peel cards and adhesive layer are disposed on the bottom of the sheet, the liners are disposed on the top.

Adhesive liner 34 is also preferably tented to allow patient blinking as previously described for the sheet. Again, this tented structure assists in eye fixation needed during the eye surgery. The function of the liner is to protect the non-surgical eye. The liners are removable and give the practitioner the flexibility to operate on one or both eyes. The liners are removably attached to the sheet by an attachment means. For example, such means include adhesives, velcro, hinges, hooks and loops, zippers, fasteners, tapes, buttons, and combinations thereof. Additionally, it is within the scope of the invention for the liners to be able to latch back onto the sheet after they are removed. For example, the liners could have velcro strips or other such fasteners that allow replacement of the liner back onto the sheet. In this situation, the practitioner can remove one liner leaving the other liner to protect the non-surgical eye. After the operation on the surgical eye, the liner can be replaced over the surgical eye. This replacement of the liner allows the practitioner to remove the liner on the other eye while providing protection to the eye just operated on during the operation of the other eye.

A method of using the dual refractive drape is as follows. The practitioner holds the drape and, if needed, will separate the drape along the first and/or second perforations to form the desired drape configuration for the specific eye surgery. One of at least sixteen different shapes and physical arrangements can be formed using the dual refractive drape. The step of removing the peel cards allows exposure of the adhesive layer. The drape is then secured on the patient using the adhesive layer. Depending on whether the surgery is single or bilateral, the adhesive liners would be removed in conjunction with exposing either one or both eyes. If both eyes are to be operated, one liner can be removed with the other liner in place over the non-surgical eye to protect it. The tenting feature of the sheet and the liner allows the patient to blink and facilitates in eye fixation that is needed during the surgery. The step of protecting the patient and surgeon from scatter rays caused by the laser is accomplished by the drape being made of a laser reflective material.

The same drape can be utilized in the procedure on the other eye by replacing the liner over the aperture of the eye that was just operated on and removing the liner over the other eye. After surgery, the drape is removed from the patient. In addition, if the surgeon desires a different draping configuration after the surgery on the eye, the drape can be reconfiguring after the removal step to another one of at least sixteen different shapes and physical arrangements to form the desired drape configuration for the specific eye surgery. The drape would then be repositioned on the patient.

The embodiments depicted in FIGS. 1–23 are intended to be merely exemplary, and are not intended to depict all possible embodiments of methods using the dual refractive drape for ophthalmic surgery. Rather, sheet 8 can have any configuration that allows the use of the dual refractive drape to be configured in many different ways for both single or bilateral eye surgical procedures while allowing coverage of the non-surgical eye and providing a clearance portion between the sheet and the patient's eye. The ability to cover the non-surgical eye in comfort in order to support eye fixation and allow the drape to be configured for many different ophthalmic surgical procedures is greatly advanced by the present invention by providing sheet 8 with the tent portion, the perforations, and the adhesive liner.

What is claimed is:

1. A method of using a dual refractive drape for eye surgery on a patient, comprising the steps of:

providing a drape of the type having a sheet including a top, a bottom, a side, a right aperture, and a left aperture therethrough; the sheet further defining at least one first perforation and at least one second perforation such that the first perforation is positioned between and about the right and the left apertures, and the second perforation is positioned such that the apertures are divided by the second perforation, the drape having a tent portion formed about the second perforation for providing a clearance portion between an eye and the drape;

holding the drape;

configuring the drape in one of at least sixteen different shapes and physical arrangements to form the desired drape configuration for the specific eye surgery; and positioning the drape on the patient such that the tent portion provides clearance between the eye and the drape.

2. The method of claim 1, further comprising the step of protecting the patient and surgeon from scatter rays and projectile debris due to laser ablation.

3. The method of claim 1, further comprising the steps of covering the non-surgical eye and allowing the patient to blink the non-surgical eye in comfort to facilitate eye fixation of the surgical eye.

4. The method of claim 1, wherein said configuration step further includes the steps of separating said sheet along said first perforation and separating said sheet along said second perforation.

5. The method of claim 1, wherein said configuration step further includes the step of separating said sheet along said first perforation.

6. The method of claim 1, wherein said configuration step further includes the step of separating said sheet along said second perforation.

7. The method of claim 1, wherein said positioning step further includes the steps of removing a peel card to allow exposure of an adhesive layer and securing said drape to the patient by said adhesive layer.

8. The method of claim 1, further including the step of removing the drape from the patient.

9. The method of claim 8, wherein said removal step further includes the steps of reconfiguring said drape to another one of at least sixteen different shapes and physical arrangements to form the desired drape configuration for the specific eye surgery and repositioning said drape on the patient.

10. The method of claim 1, further comprising the steps of removing an adhesive liner from said drape and exposing the surgical eye.

11. The method of claim 10, wherein said removal step further includes the step of replacing said adhesive liner on said drape and covering the surgical eye.

12. The method of claim 11, further comprising the steps of removing an adhesive liner from said drape and exposing the non-surgical eye.

13. The method of claim 1, further comprising the step of providing a clearance portion between the eye and said sheet to facilitate eye fixation.

14. A method of using a dual refractive drape for eye surgery on a patient, comprising the steps of:

providing a drape of the type having a sheet including a top, a bottom, a side, a right aperture, and a left aperture therethrough; the sheet further defining at least one first perforation and at least one second perforation such that the first perforation is positioned between and about the right and the left apertures, and the second perforation is positioned such that the apertures are divided by the second perforation, the drape having a tent portion formed about the second perforation for providing a clearance portion between an eye and the drape;

holding the drape;

configuring the drape in one of at least sixteen different shapes and physical arrangements to form the desired drape configuration for the specific eye surgery;

covering the non-surgical eye and allowing the patient to blink the non-surgical eye in comfort to facilitate eye fixation of the surgical eye; and positioning the drape on the patient such that the tent portion provides clearance between the eye and the drape.

15. The method of claim 14, further including the step of removing an adhesive liner.

16. The method of claim 15, wherein said removal step further includes the step of exposing the surgical eye.

* * * * *